United States Patent
Greenwood et al.

(10) Patent No.: US 9,593,126 B2
(45) Date of Patent: Mar. 14, 2017

(54) SYNTHESIS OF SPIROCYCLIC ISOXAZOLINE DERIVATIVES

(71) Applicant: Zoetis Services LLC, Florham Park, NJ (US)

(72) Inventors: Sean D. W. Greenwood, Kalamazoo, MI (US); Timothy L. Stuk, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 14/439,091

(22) PCT Filed: Nov. 20, 2013

(86) PCT No.: PCT/US2013/070959
§ 371 (c)(1),
(2) Date: Apr. 28, 2015

(87) PCT Pub. No.: WO2014/081800
PCT Pub. Date: May 30, 2014

(65) Prior Publication Data
US 2015/0291612 A1    Oct. 15, 2015

Related U.S. Application Data

(60) Provisional application No. 61/729,022, filed on Nov. 21, 2012.

(51) Int. Cl.
| | | |
|---|---|---|
| C07D 261/04 | (2006.01) | |
| C07D 491/107 | (2006.01) | |
| C07D 307/88 | (2006.01) | |
| C07D 307/94 | (2006.01) | |
| A61K 31/343 | (2006.01) | |
| A61K 31/422 | (2006.01) | |
| C07D 491/10 | (2006.01) | |
| C07C 315/04 | (2006.01) | |

(52) U.S. Cl.
CPC ........ *C07D 491/107* (2013.01); *C07C 315/04* (2013.01); *C07D 491/10* (2013.01)

(58) Field of Classification Search
CPC  C07D 261/04; C07D 491/107; C07D 307/88; C07D 307/94; A61K 31/343; A61K 31/422

USPC ........ 548/240; 514/378, 462, 469; 549/469, 549/332

See application file for complete search history.

(56) References Cited

FOREIGN PATENT DOCUMENTS

| IN | WO 2012151158 A1 * | 11/2012 | ........... C07D 413/14 |
|---|---|---|---|
| SE | WO 2012120339 A1 * | 9/2012 | ........... H04L 5/0064 |
| WO | 91/14434 | 10/1991 | |
| WO | 2004/113347 | 12/2004 | |
| WO | 2012/017359 | 2/2012 | |
| WO | 2012/120399 | 9/2012 | |

OTHER PUBLICATIONS

PCT International Search Report, PCT/US2013/070959, mailed Feb. 17, 2014 (4 pages).
Tokutake et al., "A Convenient Synthesis of 1,4-Diaryl-3-(4-toluenesulfonyl)-azetidin-2-ones from Esters and Aldimines", Synthesis, 1:66-67, 1983.
Database Registry [online] Chemical Abstracts Service, Columbus, Ohio, US, Database accession No. 1158363-70-2, 2009.

* cited by examiner

*Primary Examiner* — Alicia L Otton
*Assistant Examiner* — Sagar Patel
(74) *Attorney, Agent, or Firm* — Paul M. Misiak

(57) ABSTRACT

The invention recites an improved process for preparing spirocyclic isoxazoline derivatives of Formula (1) wherein "*", $R^{1a}$, $R^{1b}$, and $R^{1c}$ are as described herein.

(1)

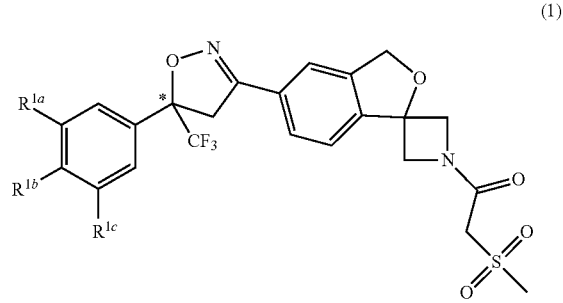

14 Claims, No Drawings

SYNTHESIS OF SPIROCYCLIC ISOXAZOLINE DERIVATIVES

FIELD OF THE INVENTION

This invention relates to an improved process for preparing spirocyclic isoxazoline derivatives having parasiticidal activity. The spirocyclic isoxazoline derivatives have exceptional activity against insects and acarids with low toxicity which makes them particularly valuable for use in domestic animals.

BACKGROUND

As described in an earlier application, WO2012/120399, the spiro-azetidine isobenzofuran derivatives were prepared using a substituent, i.e., protecting group, to block or protect the amine moiety on the compound. For example, non-limiting amine protecting groups include acyl groups, acyloxy groups, diphenylmethane, and benzylcarbamates. Removal of the BOC protecting group was accomplished under acidic conditions with subsequent coupling reactions to obtain the chiral amides. Further, the process for preparing the crystalline form of (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone is fully described in PCT/US2013/56945.

The present invention provides an improved process for preparing the methylsulfonylethanone spiro[azetidine-3,1-isobenzofuran]isoxazoline derivatives. The benzenesulfonic acid salt of the intermediate amine is neutralized and then undergoes simple coupling with a nitrophenyl sulfonylacetate reactant.

SUMMARY

The present invention describes an improved process for preparing the methylsulfonylethanone spiro[azetidine-3,1-isobenzofuran] isoxazoline derivatives of Formula 1

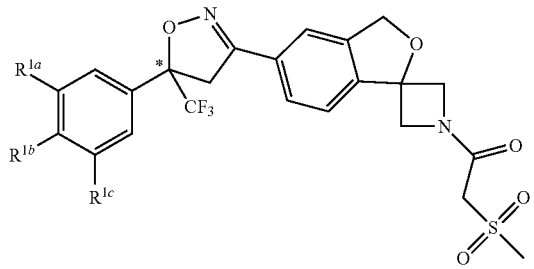

(1)

where $R^{1a}$, $R^{1b}$, and $R^{1c}$ are each independently selected from hydrogen, halogen, or $CF_3$; and "*" represents a chiral center.

In another aspect of the invention is a process for preparing a Formula (1) compound wherein $R^{1a}$, $R^{1b}$, and $R^{1c}$ are each independently halogen.

In another aspect of the invention is a process for preparing a Formula (1) compound wherein $R^{1a}$, $R^{1b}$, and $R^{1c}$ are each independently selected from fluoro and chloro.

In another aspect of the invention is a process for preparing a Formula (1) compound wherein $R^{1a}$ and $R^{1c}$ are each chloro and $R^{1b}$ is fluoro.

In another aspect of the invention is a process for preparing a Formula (1) compound wherein at least one of $R^{1a}$, $R^{1b}$ and $R^{1c}$ is $CF_3$.

In another aspect of the invention is a process for preparing a Formula (1) compound by reacting a Formula (1a) compound

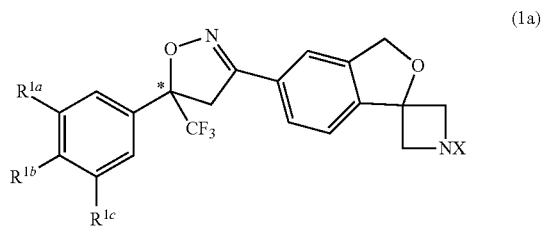

(1a)

wherein "*", $R^{1a}$, $R^{1b}$, and $R^{1c}$ are as described herein, and X is an acid addition salt, with a Formula (2) compound, in an organic solvent, wherein $R^2$ is hydrogen,

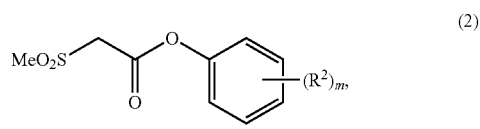

(2)

halogen, or nitro, and m is the integer 1, 2, 3, 4, or 5, and wherein at least one of $R^2$ is halo or nitro, provided that only one of $R^2$ is nitro; in the presence of a non-aqueous base.

In yet another aspect of the invention is a process for preparing a Formula (1) compound by reacting a Formula (1a) compound wherein "*", $R^{1a}$, $R^{1b}$, and $R^{1c}$ are as described herein, and a Formula (2a) compound, in an organic solvent,

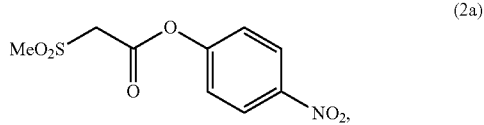 [SMILES: CS(=O)(=O)CC(=O)Oc1ccc([N+](=O)[O-])cc1]

(2a)

in the presence of a non-aqueous base.

In another aspect of the invention is a process for preparing a Formula (1) compound by reacting a Formula (1a1) compound, wherein "*" is as defined

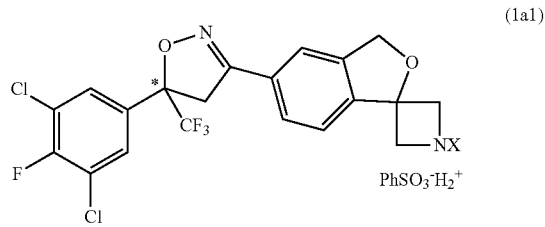

(1a1)

herein, and a Formula (2) compound, in an organic solvent, wherein $R^2$ and m are as defined herein, in the presence of a non-aqueous base.

In another aspect of the invention is a process for preparing a Formula (1) compound by reacting a Formula (1a1)

compound with a Formula (2a) compound, in an organic solvent, in the presence of a non-aqueous base.

In another aspect of the invention is a process for preparing a Formula (3) compound

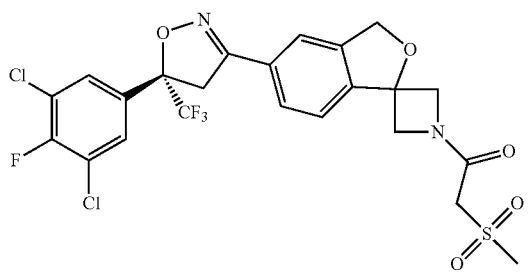

(3)

by reacting a Formula (1b1) compound

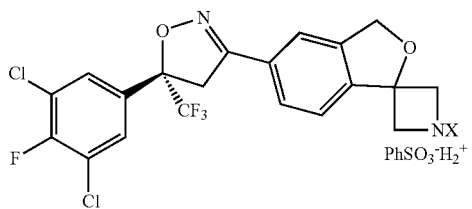

(1b1)

with the Formula (2) compound, in an organic solvent, wherein $R^2$ and m are as defined herein, in the presence of a non-aqueous base.

In another aspect of the invention is a process for preparing a Formula (3) compound by reacting a Formula (1b1) compound with a Formula (2a) compound, in an organic solvent, in the presence of a non-aqueous base.

In another aspect of the invention, non-limiting examples of the organic solvent include: isopropyl acetate, tetrahydrofuran, methyl tert-butyl ether, ethyl acetate, toluene, and the like. A preferred organic solvent is isopropyl acetate.

In another aspect of the invention, non-limiting examples of a non-aqueous base include: trialkylamines (e.g., trimethylamine, triethylamine, diisopropylethylamine, and the like), pyridine, diazaobicyclo-undec-7-ene (DBU), and the like. A preferred non-aqueous base is triethylamine.

In another aspect of the invention the Formula (1a) compound and Formula (2) compound; Formula (1a) compound and Formula (2a) compound; Formula (1a1) compound and Formula (2) compound; Formula (1a1) compound and Formula (2a) compound; Formula (1b1) compound and Formula (2) compound; and Formula (1b1) compound and Formula (2a) compound are reacted in about equimolar amounts, in an organic solvent, in the presence of a non-aqueous base.

In another aspect of the invention, the solids that precipitate out of the organic solution (i.e., isopropyl acetate) are removed and the remaining organic solution is sequentially washed at least two times with an aqueous base and then at least two times with water. Non-limiting examples of an aqueous base include hydroxides, carbonates, and the like. A preferred aqueous base is selected from sodium hydroxide, potassium hydroxide, ammonium hydroxide, sodium carbonate, potassium carbonate, sodium bicarbonate, and potassium bicarbonate. An even more preferred aqueous base is a hydroxide, for example sodium hydroxide, potassium hydroxide, and ammonium hydroxide. The organic solution is then concentrated under vacuum.

In one aspect of the invention, the concentrated organics are added to a volume of alcohol, for example, methanol, ethanol, propanol, butanol, and the like. A preferred alcohol is methanol. The methanolic solution is then slowly added to water while stirring. The resulting amorphous solids are filtered and dried.

In yet another aspect of the invention, the concentrated organics are added to a volume of a solution comprising ethyl acetate, n-heptane, and ethanol. Ethyl acetate is about 5% volume/volume, n-heptane is about 35% volume/volume, and ethanol is about 60% volume/volume. Crystal seeds of polymorphic Form A, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, are added. The mixture is cooled and the resulting crystalline solids are isolated by filtration and dried.

In another aspect of the invention is a process for preparing a Formula (2a) compound

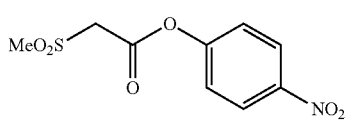

(2a)

comprising mixing methanesulfonylacetic acid, acetonitrile, and triethylamine. The reaction mixture is cooled and then p-nitrophenylchloroformate in acetonitrile is added. Water is added and the reaction mixture is filtered and washed with acetonitrile:water (1:3). The material is dried and then further purified by heating the solids to about 80° C. in isopropylacetate. The mixture is cooled, filtered, and washed with tert-butyl methyl ether. The solids are then dried under vacuum.

Alternatively, the Formula (2a) compound can be prepared by mixing methanesulfonylacetic acid, 4-nitrophenol, and acetonitrile together under nitrogen. The reaction mixture is cooled and N-(-3-dimethylaminopropyl)-N'-ethylcarbodiimide hydrochloride is added portionwise. The reaction mixture is quench with water. The solids are filtered and washed with water and then dried under vacuum.

As described above, the methylsulfonylethanone spiro [azetidine-3,1-isobenzofuran] isoxazoline derivatives of Formula 1, including the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, and the crystal polymorphic Form A of (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, can be prepared as described in WO2012/120399 and PCT/US2013/56945, respectively.

DEFINITIONS

For purposes of the present invention, as described and claimed herein, the following terms and phrases are defined as follows:

"Alcohol", as used herein, unless otherwise indicated, refers to a hydroxyl moiety having a further alkyl substituent. The alkyl portion (i.e., alkyl moiety) of the alcohol group has the same definition as below. Non-limiting examples include: methanol, ethanol, propanol, isopropanol, butanol, benzyl alcohol, and the like.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: methoxy, ethoxy, and the like.

"Alkyl", as used herein, unless otherwise indicated, refers to saturated monovalent hydrocarbon alkane radicals of the general formula $C_nH_{2n+1}$. The alkane radical may be straight or branched and may be unsubstituted or substituted. For example, the term "$(C_1$-$C_6)$alkyl" refers to a monovalent, straight or branched aliphatic group containing 1 to 6 carbon atoms. Non-exclusive examples of $(C_1$-$C_6)$ alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl moiety may be attached to the chemical moiety by any one of the carbon atoms of the aliphatic chain. Alkyl groups are optionally substituted as described herein. Further when used in compound words such as alkylphenyl, said alkyl moiety has the same meaning as herein defined and may be attached to the chemical moiety by any one of the carbon atoms of the aliphatic chain. Non-limiting examples of the compound word, alkylphenyl include: $C_1$alkylphenyl is —$CH_2$phenyl, $C_2$alkylphenyl is —$CH_2CH_2$phenyl, $C_0$phenyl is phenyl, and the like.

"Alkenyl" as used herein, unless otherwise indicated, refers to a straight or branched aliphatic hydrocarbon chain having 2- to 6-carbon atoms and containing at least one carbon-carbon double bond (for example —C═C—, or —C═$CH_2$). Non-exclusive examples of alkenyl include: vinyl, 1-propenyl, 2-propenyl, isopropenyl, 1-butenyl, 2-butenyl, 3-butenyl, 2-pentenyl, and the like.

"Alkynyl" as used herein, unless otherwise indicated, refers to straight or branched aliphatic hydrocarbon chain having 2- to 6-carbon atoms and containing at least one carbon-carbon triple bond (for example, —C≡C— or —C≡CH). Non-exclusive examples of alkynyl include: ethynyl, 2-propynyl, 1-methyl-2-propynyl, 2-butynyl, 3-butynyl, 2-methyl-3-butynyl, and the like.

"Chiral", as used herein, unless otherwise indicated, refers to the structural characteristic of a molecule that makes it impossible to superimpose it on its mirror image, (e.g., "R" and "S" enantiomers). The term is also depicted as an asterisk (i.e.,*) in the Examples and preparations and refers to a chiral center which includes both the S and R enantiomers.

"Cycloalkyl", as used herein, unless otherwise indicated, includes fully saturated or partially saturated carbocyclic alkyl moieties. Non-limiting examples of partially saturated cycloalkyls include: cyclopropene, cyclobutene, cycloheptene, cyclooctene, cyclohepta-1,3-diene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups are optionally substituted with at least one substituent. Further when used in compound words such as alkylcycloalkyl, said alkyl and cycloalkyl moiety has the same meaning as herein defined and may be attached to the chemical moiety by any one of the carbon atoms of the aliphatic chain. Examples of $C_0$-$C_6$alkyl$C_3$-$C_6$cycloalkyl include, methylcyclopropane ($C_1$alkyl$C_3$cycloalkyl or —$CH_2$cyclopropane), ethylcyclopropane ($C_2$alkyl$C_3$cycloalkyl or —$CH_2CH_2$cyclopropane), methylcyclobutane ($C_1$alkyl$C_4$cycloalkyl or —$CH_2$cyclobutane), ethylcyclobutane ($C_2$alkyl$C_4$cycloalkyl or —$CH_2CH_2$cyclobutane), methylcyclohexane ($C_1$alkyl$C_6$cycloalkyl or —$CH_2$cyclohexane), and the like. $C_0$alkyl$C_3$-$C_6$cycloalkyl is $C_3$-$C_6$cycloalkyl. Cycloalkyl moieties are optionally substituted as described herein "Halogen" or "halo", as used herein, unless otherwise indicated, refers to fluorine, chlorine, bromine and iodine. Further, when used in compound words such as "haloalkyl", "haloalkoxy", "haloalkenyl", or "haloalkynyl", said alkyl, alkoxy, alkenyl, and alkynyl may be partially or fully substituted with halogen atoms which may be the same or different and said alkyl, alkoxy, alkenyl, and alkynyl moiety has the same meaning as above and may be attached to the chemical moiety by any one of the carbon atoms of the aliphatic chain. Examples of "haloalkyl" include $F_3C$—, $ClCH_2$—, $CF_3CH_2$— and $CF_3CCl_2$—, and the like. The term "haloalkoxy" is defined analogously to the term "haloalkyl". Examples of "haloalkoxy" include $CF_3O$—, $CCl_3CH_2O$—, $HCF_2CH_2CH_2O$— and $CF_3CH_2O$—, and the like. The term "haloalkenyl is defined analogously to the term "haloalkyl" except that the aliphatic chain contains at least one carbon-carbon double bond. Examples of "haloalkenyl" include $CF_3HC$═CH—, $CCl_3HC$═CH—, and $HCF_2HC$═CH—, and the like.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O, or S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]pyridine, benzo[1,2,5]thiadiazole, and the like. The heteroaryl group may be attached to the chemical moiety by any one of the carbon atoms or nitrogen heteroatoms within the monocyclic or fused ring. Further when used in compound words such as alkylheteroaryl, said alkyl and heteroaryl moiety have the same meaning as herein defined and may be attached to the chemical moiety by any one of the carbon atoms of the aliphatic chain. For example, $C_0$alkylheteroaryl is heteroaryl, $C_1$alkylheteroaryl is —$CH_2$heteroaryl, $C_0$alkylheteroaryl is —$CH_2CH_2$heteroaryl, and the like. Heteroaryls are optionally substituted as described herein.

"Heterocycle", as used herein, unless otherwise indicated, refers to a partially saturated or saturated 3- to 7-membered monocyclic ring containing one or more heteroatoms each independently selected from N, O, or S, preferably from one to four heteroatoms. The heterocyclic ring can be part of a fused ring or spiro-ring moiety. Non-exclusive examples of heterocycle include oxirane, thiarane, aziridine, oxetane, azetidine, thiatane, tetrahydrofuran, tetrahydrothiophene, pyrrolidine, tetrahydropyrane, piperidine, piperazine, tetrahydropyridine, 2H-azirine, 2,3-dihydro-azete, 3,4-dihydro-2H-pyrrole, and the like. The heterocycle group may be attached to the chemical moiety by any one of the carbon atoms or nitrogen heteroatoms within the ring. Further when used in compound words such as alkylheterocycle, said alkyl and heterocycle moiety have the same meaning as herein defined and may be attached to the chemical moiety by any one of the carbon atoms of the aliphatic chain. For example, $C_0$alkylheterocycle is heterocycle, $C_1$alkylheterocycle is —$CH_2$heterocycle, $C_0$alkylheterocycle is —$CH_2CH_2$heterocycle, and the like. Heterocycles are optionally substituted as described herein.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from zero up to a number of available positions for substitution.

"Protecting group" or "Pg", as used herein, unless otherwise indicated, refers to a substituent that is commonly employed to block or protect an amine on the compound thereby protecting its functionality while allowing for the reaction of other functional groups on the compound "Seed(s)" or "Crystal Seed(s)", as used herein, unless otherwise indicated, refer to crystals of polymorphic Form A of (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone as described in PCT/US2013/56945.

DETAILED DESCRIPTION

The present invention provides an improved process for preparing Formula (1) compounds by reacting spiro[azetidineisobenzofuran]isoxazolines with compounds of Formula (2).

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or *Beilsteins Handbuch der organischen Chemie*, 4, Aufl. ed. Springer-Verlag, Berlin, including supplements (also available via the Beilstein online database)). For illustrative purposes, the reaction schemes depicted below demonstrate potential routes for synthesizing compounds of the present invention, and key intermediates. For a more detailed description of the individual reaction steps, see the Examples section below. A skilled artisan will appreciate that other suitable starting materials, reagents, and synthetic routes may be used to synthesize the compounds of the present invention and a variety of derivatives thereof. Further, many of the compounds prepared by the methods described below can be further modified in light of this disclosure using conventional chemistry well known to the skilled artisan.

Compounds of the present invention described herein contain at least one asymmetric or chiral center; and, therefore, exist in different stereoisomeric forms. The R and S configurations are based upon knowledge of known chiral inversion/retention chemistry. Unless specified otherwise, it is intended that all stereoisomeric forms of the compounds of the present invention as well as mixtures thereof, including racemic mixtures and diastereomeric mixtures, form part of the present invention.

Enantiomeric mixtures can be separated into their individual enantiomers on the basis of their physical chemical differences by methods well known to those skilled in the art, such as chromatography and/or fractional crystallization. A more detailed description of techniques that can be used to resolve stereoisomers of compounds from their racemic mixture can be found in Jean Jacques Andre Collet, Samuel H. Wilen, Enantiomers, Racemates and Resolutions, John Wiley and Sons, Inc. (1981).

Compounds of this invention can exist as one or more stereoisomers. The various stereoisomers include enantiomers, diastereomers and atropisomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereo isomers or as an optically active form. For example, two possible enantiomers of Formula 1 are depicted as Formula (a) (S-isomer) and Formula (b) (R-isomer) involving the isoxazoline chiral center. Molecular depictions drawn herein follow standard conventions for depicting stereochemistry. The variables $R^{1a}$, $R^{1b}$, $R^{1c}$, and X are as defined herein.

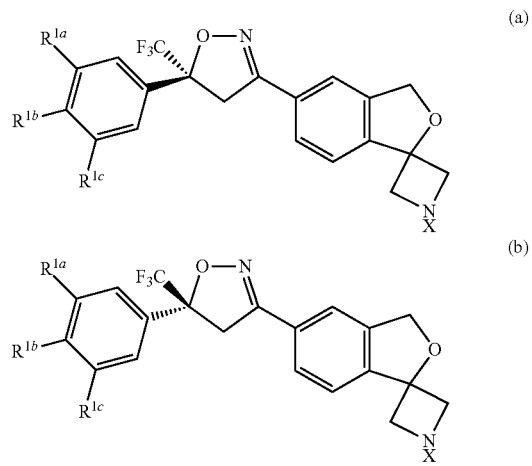

For illustrative purposes, the reaction schemes depicted below demonstrate potential routes for synthesizing key intermediates and compounds of the present invention. For a more detailed description of the individual reaction steps, see the Examples section below. Those skilled in the art will appreciate that other suitable starting materials, reagents, and synthetic routes may be used to synthesize the intermediates and compounds of the present invention and a variety of derivatives thereof. Further, many of the compounds prepared by the methods described below can be further modified in light of this disclosure using conventional chemistry. Scheme 1 outlines the general procedures useful for the preparation and isolation of compounds of the present invention. It is to be understood, however, that the invention, as fully described herein and as recited in the claims, is not intended to be limited by the details of the following schemes or modes of preparation.

In the preparation of compounds of the present invention, protection of remote functionality of intermediates from undesired reactions can be accomplished with a protecting group. For example, an amine-protecting group is a substituent attached to an amine that blocks or protects the amine-functionality of the compound or intermediate. Suitable amine protecting groups include: acyl groups (e.g., formyl, acetyl, chloroacetyl, trichloro-acetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like); and acyloxy groups (e.g., 1-tert-butyloxycarbonyl (Boc), methoxycarbonyl, 9-fluorenyl-methoxycarbonyl, 2,2,2-trifluoroethoxy-carbonyl, 2-trimethylsilylethxoycarbonyl, vinyloxycarbonyl, allyloxycarbonyl, 1,1-dimethyl-propynyloxycarbonyl, benzyloxy-carbonyl, p-nitrobenzyloxycarbonyl, 2,4-dichlorobenzyloxycarbonyl, and the like), diphenylmethane, and benzylcarbamates. Similarly, diphenylmethane and benzylcarbamates can be used as amine protecting groups. Suitable protecting groups and their respective uses are readily determined by one skilled in the art. For a general description of protecting groups and their use, see T. W. Greene, *Protective Groups in Organic Synthesis*, John Wiley & Sons, New York, 1991.

Scheme 1-Chiral synthesis

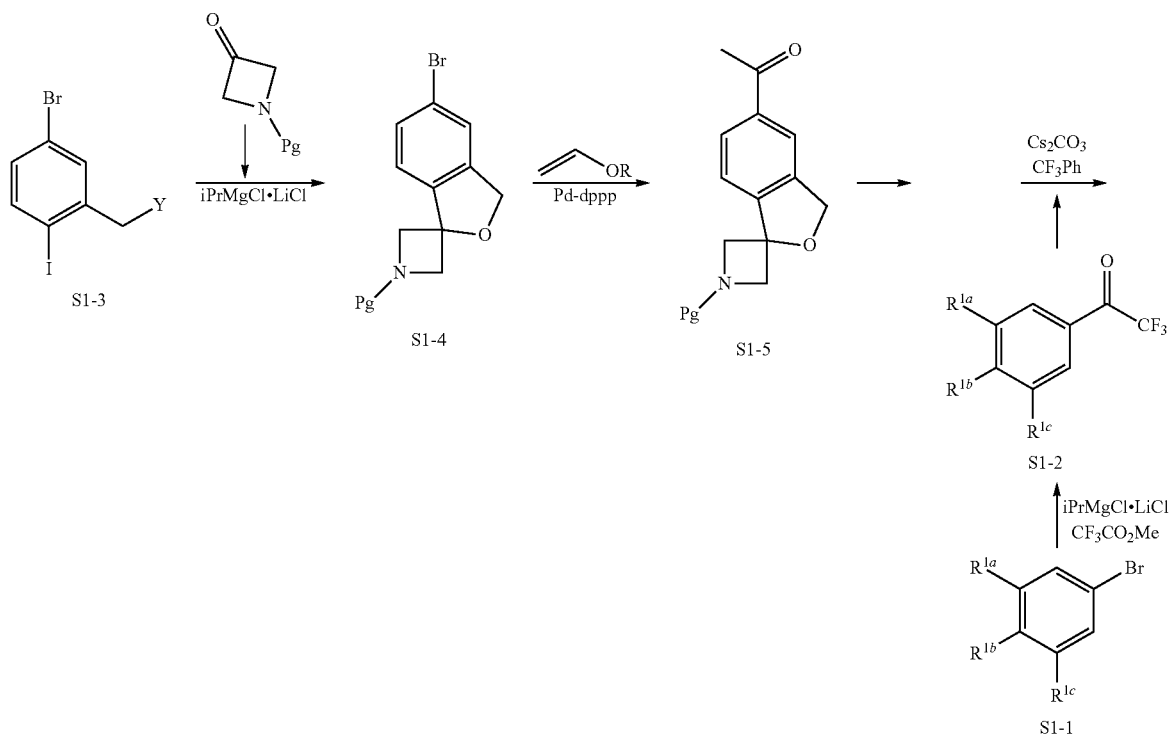

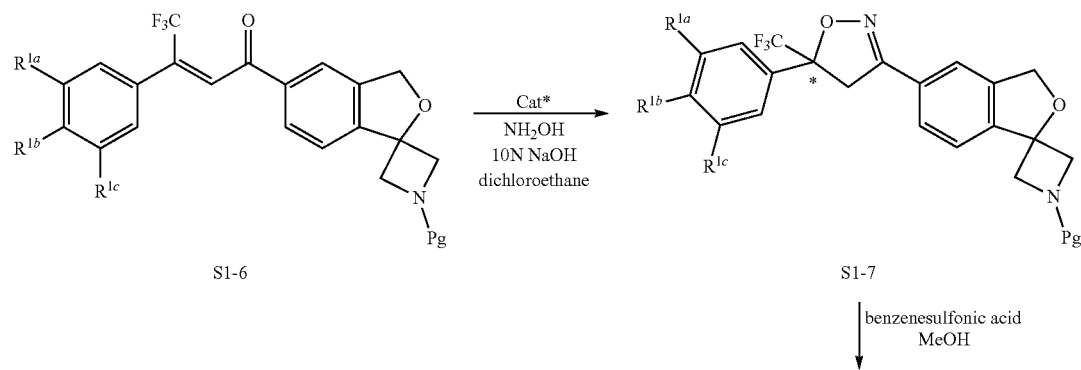

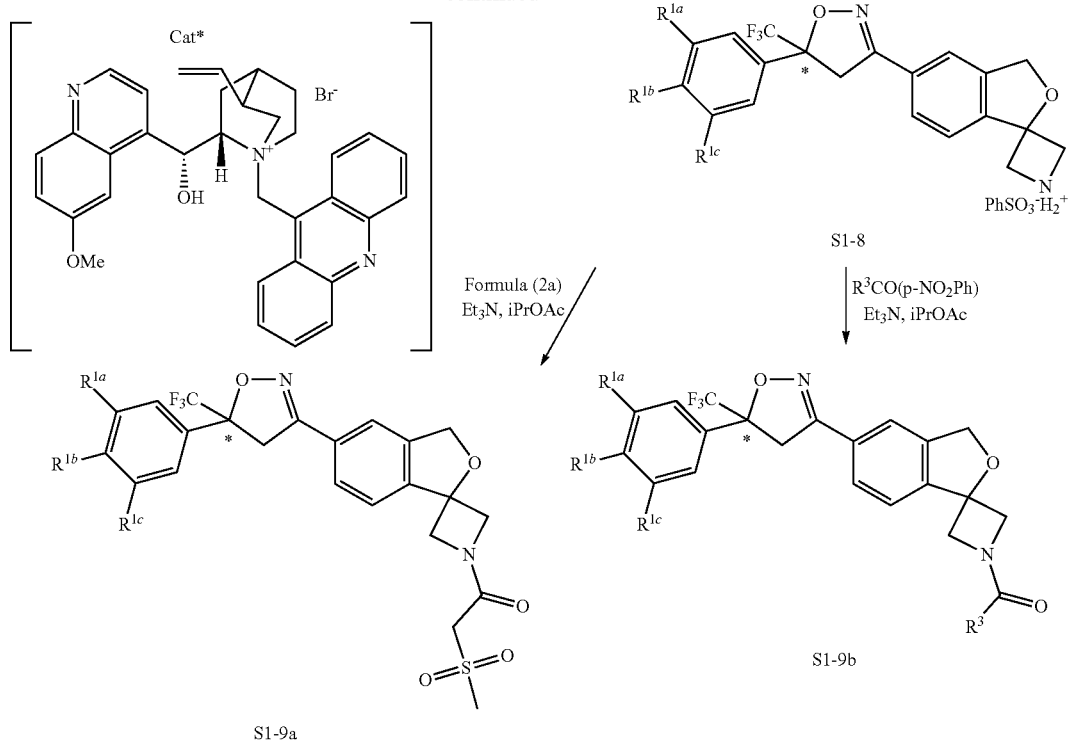

-continued

S1-9a

S1-9b $R^{1a}$, $R^{1b}$, and $R^{1c}$ are as defined herein. In Scheme 1, the R substituent depicts a $C_1$-$C_6$alkyl moiety (e.g., methyl, ethyl, propyl, isopropyl, butyl, and the like). The $R^3$ substituent depicts hydrogen, $C_1$-$C_6$alkyl, $C_2$-$C_6$alkenyl, $C_0$-$C_6$alkyl$C_3$-$C_6$-cycloalkyl, $C_0$-$C_6$alkylphenyl, $C_0$-$C_6$alkylheteroaryl, or $C_0$-$C_6$alkylheterocycle; wherein each $R^3$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$$C_1$-$C_6$alkyl, —SH, —S(O)$_p$NR$^a$R$^b$, —NR$^a$R$^b$, —NR$^a$C(O)R$^b$, —SC(O)R, —SCN, or —C(O)NR$^a$R$^b$; wherein R$^a$ is hydrogen, $C_1$-$C_6$alkyl, or $C_0$-$C_3$alkyl$C_3$-$C_6$cycloalkyl, wherein the R$^a$ alkyl and alkylcycloalkyl is optionally substituted by cyano or at least one halo substituent; R$^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each R$^b$ can be optionally substituted, where chemically possible, with at least one substituent selected from hydroxyl, cyano, halo, or —S(O)$_p$$C_1$-$C_6$alkyl; and wherein $R^3$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, hydroxyl, $C_1$-$C_6$alkoxy, hydroxyl$C_1$-$C_6$alkyl-, $C_1$-$C_6$alkyl, $C_1$-$C_6$haloalkyl, —SH, —S(O)$_p$ $C_1$-$C_6$alkyl, and $C_1$-$C_6$haloalkoxy; p is the integer 0, 1, or 2. Pg is a protecting group, for example Boc, diphenylmethane, or a benzylcarbamate and Y can be bromine, chlorine, iodine, hydroxyl, or a sulfonate leaving group. The asterisk (*) depicts a chiral center, (i.e., (R) or (S) stereochemistry).

A chiral synthesis of the compounds described within can be achieved according to Scheme 1. From the iodobromobenzyl derivative (S1-3), Grignard formation and condensation with tert-butyl 3-oxoazetidine-1-carboxylate provides the cyclized tert-butyl 5'-bromo-3'H-spiro[azetidine-3,1'-isobenzofuran]-1-carboxylate (S1-4) in a one-pot reaction or a step-wise fashion. Palladium catalyzed condensation with a vinyl ether provides the acetophenone (S1-5) which can undergo condensation with the trifluoroacetophenone (S1-2) to give the chalcone (S1-6). Addition of hydroxylamine and cyclization in the presence of a chiral catalyst (Cat*) provides the desired enantiomer of the isoxazoline (S1-7). Removal of the Boc protecting group can be achieved under acidic conditions such as benzene sulfonic acid in methanol to provide the chiral azetidine (S1-8) which can undergo couplings as previously described to provide the chiral compounds (S1-9a and S1-9b).

When the compounds of the present invention possess a free base form, for example, non-protected Formula (S1-8) compounds; wherein the Pg group is displaced with an acid addition salt ("X"), the compounds can be prepared as an acid addition salt by reacting the free base form of the compound with an acceptable inorganic or organic acid, e.g., hydrohalides such as hydrochloride, hydrobromide, hydrofluoride, hydroiodide; other mineral acids and their corresponding salts such as sulfate, nitrate, phosphate; and alkyl and monoarysulfonates such as ethanesulfonate, toluenesulfonate, and benzene sulfonate; and other organic acids and their corresponding salts such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include sulfate, pyrosulfate, bisulfate, sulfite, bisulfite, nitrate, phosphate, monohydrogenphosphate, dihydrogenphosphate, metaphosphate, pyrophosphate, trifluoroacetate, propionate, caprylate, isobutyrate, oxalate, malonate, succinate, suberate, sebacate, fumarate, acetate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are salts of amino acids such as arginate, gluconate, galacturonate, and the like. See, e.g., Berge S. M., et al., Pharmaceutical Salts, *J. Pharm. Sci.*, 66:1 (1977).

One skilled in the art will recognize that, in some cases, after the introduction of a given reagent as it is depicted in the schemes, it may be necessary to perform additional routine synthetic steps not described in detail to complete the synthesis of Formula (1) and Formula (2) compounds.

The skilled person will appreciate that the compounds of the present invention could be made by methods other than those herein described as incorporated herein by reference, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., *J. Org. Chem.*, 43, 2923, (1978) was performed using silica gel (RediSep Rf) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography (TLC), recrystallization, and differential (i.e., liquid-liquid) extraction techniques.

The compound structures in the examples below were confirmed by one or more of the following methods: proton magnetic resonance spectroscopy, and mass spectroscopy. Proton magnetic resonance ($^1$H NMR) spectra were determined using a Bruker spectrometer operating at a field strength of 400 megahertz (MHz). Chemical shifts are reported in parts per million (ppm, δ) downfield from an internal tetramethylsilane standard. Mass spectra (MS) data were obtained using Agilent mass spectrometer with atmospheric pressure chemical ionization. Method: Acquity UPLC with chromatography performed on a Waters BEH C18 column (2.1×50 mm, 1.7 μm) at 50° C. The mobile phase was a binary gradient of acetonitrile (containing 0.1% trifluoroacetic acid) and water (5-100%).

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

The following intermediates and example provide a more detailed description of the process conditions for preparing Formula (1) compounds. It is to be understood, however, that the invention, as fully described herein and as recited in the claims, is not intended to be limited by the details of the scheme or modes of preparation as described herein.

Intermediate 1.
(4-nitrophenyl)-2-methylsulfonylacetate (Formula (2a))

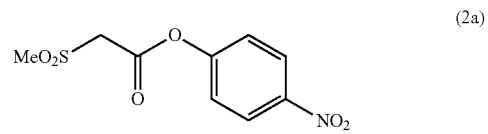

(2a)

Add 100.0 g methanesulfonylacetic acid (724 mmol) to 500 mL of acetonitrile. Add triethylamine (3.78 grams, 724 mmol) and cool the reaction to 0° C. Slowly add a solution of p-nitrophenylchloroformate (161 g, 1.08 equivalents) in 240 mL acetonitrile at a temperature of <5° C. Stir at about 5-10° C. for 15 minutes after addition. Add 1500 mL water and stir the resulting slurry for 15 minutes. Filter and wash with a solution of 25% acetonitrile in water. Dry the material. The material is further purified by heating to 80° C. in isopropyl acetate (835 mL). Cool the mixture to 20° C. over two hours and isolate the product by filtration. Wash the filter cake with 200 mL tert-butyl methyl ether. Dry the material under vacuum at 50° C. to afford 147 grams (78%) of a white solid. $^1$H NMR (CDCl$_3$, 600 MHz) 8.35 (d, 2H), 7.37 (d, 2H), 4.28 (s, 2H), 3.23 (s, 3H). MS M+1=260.

Alternatively, (4-nitrophenyl)-2-methylsulfonylacetate can be prepared by stirring methanesulphonylacetic acid (59 g), 4-nitrophenol (119 g), and acetonitrile (600 mL), under nitrogen. Cool the mixture in an ice/water bath to an internal temperature of about 3° C. Add N-(3-dimethylaminopropyl)-N'-ethylcarbodiimide hydrochloride (EDAC, 100 g) portionwise over 30 minutes. The internal temperature rises to a maximum of about 8° C. during the addition. Allow the reaction to cool to about 1-3° C. while stirring for 1 hour. Quench the reaction mixture by adding water (1200 mL) over 15 minutes at a maximum temperature of 10° C. Stir the mixture in the ice/water bath for 1-hour. Isolate the product by filtration. The yellow filter cake was washed with water until the liquors ran colorless. The filter cake was dried at 50° C. under vacuum to afford 79 g (71% yield) of a white solid. $^1$H NMR (CDCl$_3$, 600 MHz) 8.35 (d, 2H), 7.37 (d, 2H), 4.28 (s, 2H), 3.23 (s, 3H). MS M+1=260.

Intermediate 2. Chiral-5'-(5-(3,5-dichloro-4-fluorophenyl)-5-(trifluoromethyl)-4,5-dihydroisoxazol-3-yl)-3'H-spiro[azetidine-3,1'-isobenzofuran]benzene sulfonate (Formula (1a1))

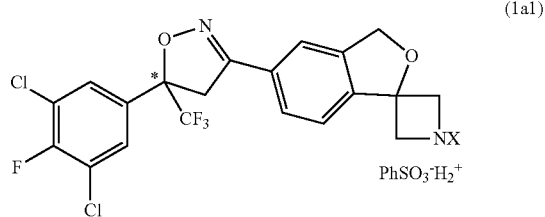

(1a1)

The compound was prepared similarly to that in Preparation 31 of WO2012/120399, except that the p-toluene sulfonic acid was replaced with benzene sulfonic acid. Chiral-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate (195 g, 348 mmol) was dissolved in methanol (600 mL) at 60° C. Benzenesulfonic acid (66.7 g, 418 mmol) was added to the reaction over 30 minutes as a solution in methanol (60 mL). The reaction was stirred at 60° C. for thirty minutes and then tert-butylmethyl ether (455 mL) was added. The reaction was cooled to 20° C. and was filtered to isolate the product. The product was washed with tert-butylmethyl ether (200 mL) and was dried to afford 167.4 g (92%) of a white powder. $^1$H NMR, 600 MHz (d$_6$-DMSO) d ppm: 9.08 (br s, 1H), 8.89 (d, 1H), 7.95 (d, 1H), 7.83 (m, 3H), 7.72 (s, 1H), 7.62 (d, 2H), 7.33 (m, 3H), 5.13 (s, 2H), 4.36 (m, 6H), 2.25; m/z (CI) 461 [M+H] (free amine). The asterisk (*) depicts the chiral center.

Example 1

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (Formula (3))

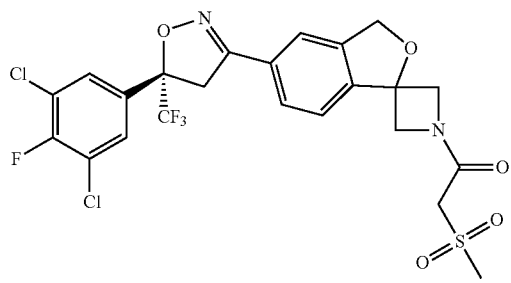 [SMILES: CS(=O)(=O)CC(=O)N1CC2(C1)OCc1cc(C3=NO[C@@](c4cc(Cl)c(F)c(Cl)c4)(C(F)(F)F)C3)ccc12]

A slurry of (S)-5'-(5-(3,5-dichloro-4-fluorophenyl)-5-trifluoromethyl)-4,5-dihydroisoxazol-3-yl)-3'H-spiro[azetidine-3,1'-isobenzofuran]benzene sulfonate (Intermediate 2, 50.0 g) and (4-nitrophenyl)-2-methylsulfonylacetate (Intermediate 1, 22.4 g, 1.07 equivalents) in isopropyl acetate (450 mL) was cooled to about 7° C. Besides isopropyl acetate, alternate non-limiting organic solvents can be used, for example: tetrahydrofuran, ethyl acetate, toluene, methyl tert-butyl ether, and the like. To this was added triethylamine (9.26 g, 1.10 equivalents). The reaction was stirred for 15 minutes at about 5-10° C. and then at about 20° C. for two hours. The solids which formed were removed by filtration. The remaining organic solution was washed sequentially with 6N aqueous ammonium hydroxide (2×250 mL) and then with water (2×200 mL). Besides ammonium hydroxide, alternate non-limiting aqueous bases can be used, for example: carbonates and other hydroxides (e.g., sodium hydroxide and potassium hydroxide), and the like. The washed organics were concentrated under vacuum to a small volume. The concentrated organics were then added to 300 mL methanol. The methanolic solution was added slowly to 20° C. water (300 mL) while stirring over 30 minutes. After stirring for an additional 15 minutes, the solids were isolated by filtration. The resulting white powder was dried under vacuum at 50° C. to a final yield of 38 g. Alternatively, the crystal form of the product can be isolated by adding the concentrated organics to a solution (300 mL) containing ethyl acetate (5%), n-heptane (35%) and ethanol (60%). The reaction mixture was heated to about 60° C. and then cooled to about 45° C. over a period of about 15-20 minutes. Crystal seeds of (S)-1-(5'-(5-(3,5-dichloro-4-fluorophenyl)-5-(trifluoromethyl)-4,5-dihydroisoxazol-3-yl)-TH-spiro[azetidine-3,1'-isobenzofuran]-1-yl)-2-(methylsulfonyl)ethanone were added to the mixture. [The crystal seeds were made by dissolving amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone in methanol and allowing vapor diffusion of an outer layer of diisopropyl ether to slowly convert the amorphous form to the crystal form over a period of about 5 days at room temperature.] The reaction mixture was maintained at about 45° C. for about 2 hours then cooled to about 30° C. at a rate of about 1.5° C. per hour, then cooled to 10° C. over three hours, linearly, then held at 10° C. for about 4.5 hours. The white slurry was cooled to about 0-1° C. over 20 minutes and held overnight (approximately 23 hours) at about 0-1° C. The product was isolated by filtration and dried. $^1$H NMR, 600 MHz (d$_6$-DMSO): 7.88 (d, 2H), 7.82 (d, 1H), 7.73 (m, 2H), 5.18 (s, 2H), 4.62 (dd, 2H), 4.42 (dd, 2H), 4.28 (m, 4H), 3.20 (s, 3H). MS: M+H=582.

We claim:

1. A process for preparing a Formula (1), compound

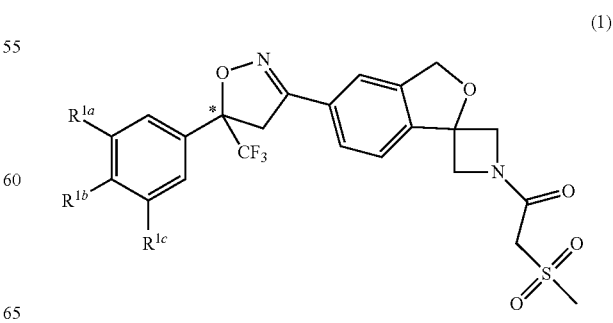

(1)

by
a) reacting a Formula (1a) compound

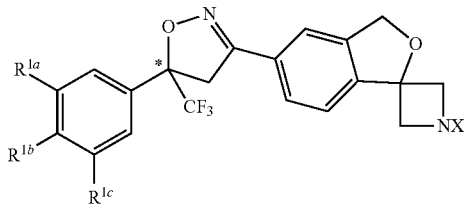

wherein $R^{1a}$, $R^{1b}$, and $R^{1c}$ are each Cl, F, and Cl, respectively; X is benzene sulfonic acid; and "*" represents a chiral center;
b) with a Formula (2) compound

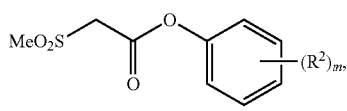

wherein $R^2$ is nitro and m is the integer 1; in an organic solvent, and in the presence of a non-aqueous base.

2. The process of claim 1, wherein Formula (2) compound is a compound of Formula (2a)

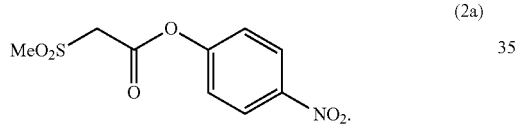

3. The process of claim 2, wherein the organic solvent is selected from the group consisting of isopropyl acetate, tetrahydrofuran, methyl tert-butyl ether, ethyl acetate, and toluene.

4. The process of claim 3, wherein the non-aqueous base is triethylamine.

5. The process of claim 4, wherein
a) equimolar amounts of the Formula (1a) compound and Formula (2a) compound are reacted in isopropyl acetate;
b) the solids are removed and the organics sequentially washed with an aqueous base and water; and
c) the organics are concentrated.

6. The process of claim 5, further comprising:
a) addition of alcohol to the concentrated organics;
b) slowly adding the alcohol solution to water while stirring; and
c) filter and dry the resulting solids.

7. The process of claim 5, wherein the concentrated solids are washed twice with an aqueous base selected from a hydroxide or carbonate and then washed twice with water.

8. The process of claim 7, wherein the aqueous base is selected from sodium hydroxide, potassium hydroxide, or ammonium hydroxide.

9. The process of claim 6, wherein the alcohol is methanol.

10. The process of claim 5, further comprising:
a) the concentrated organics are added to a solution comprising ethyl acetate, n-heptane, and ethanol;
b) add crystal seeds to the solution and cool; and
c) filter and dry the resulting solids.

11. A process for preparing a Formula (3) compound

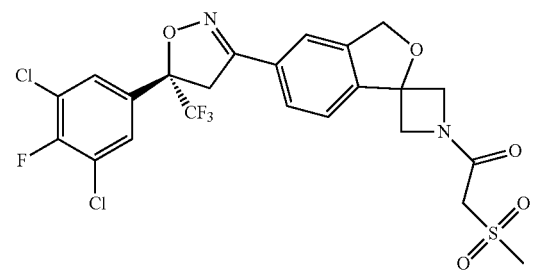

by reacting a Formula (1b1) compound with a Formula (2) compound, in an organic solvent, and in the presence of a non-aqueous base,

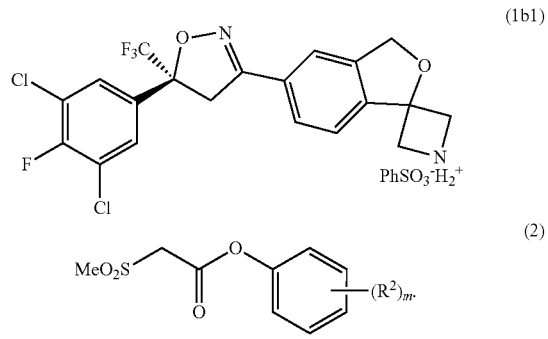

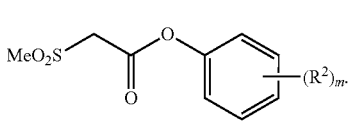

wherein $R^2$ is nitro and m is the integer 1.

12. The process of claim 11, wherein the Formula (2) compound is a compound of Formula (2a)

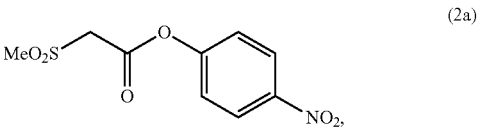 [SMILES: CS(=O)(=O)CC(=O)Oc1ccc([N+](=O)[O-])cc1]

and the organic solvent is selected from the group consisting of isopropyl acetate, ethyl acetate, toluene, tetrahydrofuran, and methyl tert-butyl ether; and the non-aqueous base is triethylamine.

13. The process of claim 12, wherein the organic solvent is isopropyl acetate, remove the solids, sequentially wash the organics with an aqueous base and water, and concentrate the organics.

14. The process of claim 13, wherein the concentrated organics are either added to methanol, slowly mixed with water, and the resulting solids isolated by filtration and dried; or the concentrated organics are added to a solution comprising ethyl acetate, n-heptane, and ethanol, then mixed with crystal seeds, allowed to cool, and the resulting solids isolated by filtration and dried.

* * * * *